(12) United States Patent
Hua et al.

(10) Patent No.: US 8,858,767 B2
(45) Date of Patent: Oct. 14, 2014

(54) POLYAMIC ACID AND ELECTRODE FOR DETECTING HYDROGEN PEROXIDE

(75) Inventors: Mu-Yi Hua, Taoyuan County (TW); Yaw-Terng Chern, Tapei (TW); Hsiao-Chien Chen, Taichung (TW); Rung-Ywan Tsai, Hsinchu County (TW)

(73) Assignee: Chang Gung University, Tao-Yuan (TW)

( * ) Notice: Subject to any disclaimer, the term of this patent is extended or adjusted under 35 U.S.C. 154(b) by 99 days.

(21) Appl. No.: 13/445,140

(22) Filed: Apr. 12, 2012

(65) Prior Publication Data

US 2013/0270112 A1     Oct. 17, 2013

(51) Int. Cl.
| | |
|---|---|
| *G01N 27/30* | (2006.01) |
| *C25B 11/04* | (2006.01) |
| *C25B 11/03* | (2006.01) |
| *C07D 277/62* | (2006.01) |
| *C07D 263/62* | (2006.01) |

(52) U.S. Cl.
CPC ............ *G01N 27/30* (2013.01); *C25B 11/0489* (2013.01); *C25B 11/0478* (2013.01); *C07D 277/62* (2013.01); *C07D 263/62* (2013.01)
USPC ....... 204/400; 204/290.11; 548/156; 548/219

(58) Field of Classification Search
CPC ........ G01N 27/30; C25B 11/03; C25B 11/04; C07D 277/62; C07D 63/622
USPC ........ 205/777.5; 204/403.01–403.14, 290.11, 204/284, 400; 427/58; 548/156, 219
See application file for complete search history.

(56) References Cited

PUBLICATIONS

Hua et al. (Biomaterials 32, 2011, 4885-4895).*
Mikroyannidis (Macromolecules 1995, 28, 5177-5183).*
Toiserkani (Polymers for Advanced Technologies Nov. 2011, 22/11, 1494-1501).*

* cited by examiner

*Primary Examiner* — Luan Van
*Assistant Examiner* — Steven Rosenwald
(74) *Attorney, Agent, or Firm* — Cesari and McKenna, LLP (57) ABSTRACT

This invention is directed to a polyamic acid represented by the following formula (I), and an electrode having an active layer made from the polyamic acid of formula (I).

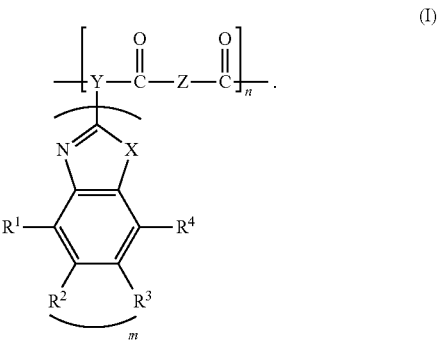

9 Claims, 6 Drawing Sheets

POLYAMIC ACID AND ELECTRODE FOR DETECTING HYDROGEN PEROXIDE

BACKGROUND OF THE INVENTION

1. Field of the Invention

This invention relates to polyamic acid, and an electrode having an active layer made from the polyamic acid, in which the polyamic acid is used to detect hydrogen peroxide.

2. Description of the Related Art

Hydrogen peroxide ($H_2O_2$) is a reactive oxygen species and a byproduct of several types of oxidative metabolism. Because the accurate determination of $H_2O_2$ is of practical importance in the clinical, environmental and industrial fields, increasing interest has focused on fabrication of reliable $H_2O_2$ biosensors. Due to their high selectivity and sensitivity, electrochemical devices have been used extensively to detect $H_2O_2$.

In electrochemical devices, electrodes used to detect analytes are either enzyme-based or enzyme-free electrodes. Enzyme-free electrodes can be made by forming an active layer on a conductor. The materials for the active layer can be inorganic materials (i.e., metallic nano-particles, metallic oxides, transition metals, carbon nanotubes, etc.), organic materials (i.e., polyamic acid, polyaniline, poly(aniline-co-p-aminophenol)) or organic-inorganic materials (i.e., polyaniline-carbon nanotubes).

As to an electrochemical device using the enzyme-free electrode, an oxidation potential (approximately 0.5 V to 0.7 V) is usually measured in this device to determine the amount of hydrogen peroxide. Since the oxidation potential is susceptible to interference with other undesired substances, such as uric acid (UA) and ascorbic acid (AA), in a test sample, the specificity for hydrogen peroxide is reduced and the accuracy of the test result would be adversely affected. Therefore, improvements for the electrodes of the electrochemical devices are aimed at detecting $H_2O_2$ at low potential while eliminating the interference of interfering molecules.

An imine group of an aromatic ring (such as pyridine) can be oxidized by $H_2O_2$ in an aqueous acetic acid solution to form N-oxide (see the following reaction formula). Therefore, electrodes that are made from materials modified with imidazole, thiazole, or oxazole are suitable to detect $H_2O_2$ or peroxy acid in the presence of acetic acid.

The inventors of the present invention have disclosed using poly (N-butyl benzimidazole)-modified gold electrode for the detection of hydrogen peroxide [*Analytica Chimica Acta* 2011, 693, 114-120]. The modified electrode detects hydrogen peroxide in the presence of carboxylic acid. The modified electrode has a detection range of 12.5 μM~5.0 mM, with a sensitivity of 419.4 μA/mM·cm², and response time of 6.3 seconds.

Accordingly, the detection of hydrogen peroxide using an electrochemical device would be ideal when the detection thereof occurs at low potential or under reduction potential without electrochemical reaction of other undesired analytes. In addition, the electrochemical device should have a short response time and high sensitivity.

SUMMARY OF THE INVENTION

According a first aspect of the present invention, there is provided a polyamic acid represented by the following formula (I):

wherein in formula (I), Z in each occurrence indicates in which R in each occurrence is hydrogen, a phenyl group, or a $C_1$ to $C_{12}$ alkyl group; bond a in each occurrence being at position 4 or 5; bond b in each occurrence being at position 4' or 5';

M being —S—, —O—, —CH$_2$—, wherein $R^5$ is —$SO_3H$, or a $C_1$ to $C_{12}$ alkyl group;
m being 1 or 2, when m is 1, Y is when m is 2, Y is X being O or S;

$R^1$, $R^2$, $R^3$, and $R^4$ in each occurrence being independently hydrogen, a $C_1$ to $C_{12}$ alkyl group, a $C_1$ to $C_{12}$ alkoxy group, a $C_1$ to $C_{12}$ ether group, a $C_1$ to $C_{12}$ cyclic alkoxy group, halogen atom, a $C_1$ to $C_{12}$ haloalky group, a hydroxyl group, a trifluoromethoxy group, a trifluoromethyl group or a phenyl group; and n being an integer ranging from 5 to 1000.

According a second aspect of the present invention, an electrode for an electrochemical device comprises a conductor, and an active layer that is formed on the conductor and that includes polyamic acid described in the aforesaid first aspect of the invention.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

A polyamic acid according to the present invention is represented by the following formula (I):

wherein in formula (I), Z in each occurrence indicates in which R in each occurrence is hydrogen, a phenyl group, or a $C_1$ to $C_{12}$ alkyl group; bond a in each occurrence being at position 4 or 5; bond b in each occurrence being at position 4' or 5'.

M is —S—, —O—, —CH$_2$—, wherein R$^5$ is —SO$_3$H, or a C$_1$ to C$_{12}$ alkyl group.

m is 1 or 2, when m is 1, Y is when m is 2, Y is

X is O or S.

R$^1$, R$^2$, R$^3$, and R$^4$ in each occurrence is independently hydrogen, a C$_1$ to C$_{12}$ alkyl group, a C$_1$ to C$_{12}$ alkoxy group, a C$_1$ to C$_{12}$ ether group, a C$_1$ to C$_{12}$ cyclic alkoxy group, halogen atom, a C$_1$ to C$_{12}$ haloalky group, a hydroxyl group, a trifluoromethoxy group, a trifluoromethyl group or a phenyl group.

n is an integer ranging from 5 to 1000.

Preferably, in formula (I), Z is

Preferably, in formula (I), m is 2 and Y is

Preferably, in formula (I), R$^1$, R$^2$, R$^3$, and R$^4$ are hydrogen.

A preferred embodiment of the polyamic acid according to this invention is represented by the following formula (I-1), i.e., polyamic acid-benzothiazole (hereinafter referred to as "PAA-BT"):

(I-1)

In formula (I-1), n and bonds a and b have the same definitions as those in formula (I).

Another preferred embodiment of the polyamic acid according to this invention is represented by the following formula (I-2), i.e., polyamic acid-benzoxazole (hereinafter referred to as "PAA-BO"):

(I-2)

In formula (I-2), n and bonds a and b have the same definitions as those in formula (I).

The polyamic acid can be prepared by well-known methods, e.g., by reacting a diamine compound having heterocyclic branch group (as shown in formula (A)) and diacid anhydride (as shown in formula (B)).

In formulas (A) and (B), $R^1$, $R^2$, $R^3$, $R^4$, X, Y, m, and M have the same definition as those in formula (I).

Examples of formula (A) include, but are not limited to, 2,2'-bis(2-benzothiazole)-4,4'-diaminobiphenyl, (DAB-PBT), 2,2'-bis(2-benzoxazole)-4,4'-diaminobiphenyl, (DAB-PBO) and 4-(2-benzothiazole)-4,4'-diamino-triphenylamine.

An example of formula (B) is, but should not be limited to, 4,4'-oxydiphthalic anhydride.

The present invention also discloses an electrode used in an electrochemical device. The electrode comprises a conductor, and an active layer formed on the conductor and including the polyamic acid of formula (I). In a preferred embodiment of the present invention, the conductor is gold (Au).

The active layer has nano-meter pores.

The electrode is used to detect hydrogen peroxide or oragnic peroxy acid. Example of organic peroxy acid is percarboxylic acid. In a preferred embodiment of the present invention, the electrode is used to detect hydrogen peroxide. In addition, the electrode can detect other molecules of interest under the presence of a suitable oxidase.

A three-step mechanism by which the electrochemical device detects $H_2O_2$ is proposed:
1. $H_2O_2$ chemically oxidizes the carboxylic group on polyamic acid to form peroxy acid.
2. The peroxy acid of polyamic acid chemically oxidizes imino group of polyamic acid to form imine-N-oxide on the polyamic acid.
3. The imine-N-oxide reverts to an imino group on the polyamic acid by electrochemical reduction.

EXAMPLES

This invention will be further described by way of the following examples. However, it should be understood that the following examples are solely intended for the purpose of illustration and should not be construed as limiting the invention in practice.

Preparation Example 1

Synthesis and Characterization of Polyamic Acid-Benzothiazole (PAA-BT)

To synthesize PAA-BT, 1.32 mmole (0.410 g) of 4,4'-oxydiphthalic anhydride (purchased from TCI company) were added to a stirred solution of 2,2'-bis(2-benzothiazole)-4,4'-diaminobiphenyl (DABPBT, 1.32 mmol, 0.595 g, made according to the procedure disclosed in *Macromolecules*, 2008, 41, 9556-9564) in N-methyl-2-pyrrolidone (NMP, purchased from Tedia company) (15% [w/v]) under $N_2$ for 6 h at room temperature, thus obtaining a resultant product of PAA-BT.

To characterize PAA-BT, FT-IR and $^1H$ NMR were used. The FT-IR spectra of PAA-BT showed absorptions at 3300 $cm^{-1}$ (N—H and O—H stretching of polyamic acid), and at 1722 $cm^{-1}$ and 1670 $cm^{-1}$ (C=O stretching of polyamic acid), thus confirming the resultant product as having characteristics of the polyamic acid group. $^1H$ NMR of PAA-BT performed in DMSO-$d_6$ detected chemical shifts at 7.23-7.60 (10H), 7.82-8.06(8H), 8.79(2H) and 10.9-11.2 ppm (2H, NH), thus confirming successful synthesis of PAA-BT. The inherent viscosity of PAA-BT was 1.21 dL/g at a concentration of 0.5 g/dL in NMP at 30° C.

Preparation Example 2

Synthesis and Characterization of Polyamic Acid-Benzoxazole (PAA-BO)

To synthesize PAA-BO, 2.06 mmole (0.638 g) of 4,4'-oxydiphthalic anhydride were added to a stirred solution of 2,2'-bis(2-benzoxazole)-4,4'-diaminobiphenyl (DABPBO, 2.06 mmol, 0.862 g, made according to the procedure disclosed in *Macromolecules*, 2008, 41, 9556-9564) in N-methyl-2-pyrrolidone (NMP) (15% [w/v]) under $N_2$ for 6 h at room temperature, thus obtaining a resultant product of PAA-BO.

The characterization of PAA-BO was similar to that of PAA-BT from <Preparation Example 1>, except that $^1H$ NMR of PAA-BO performed in DMSO-$d_6$ detected chemical shifts at 7.23-7.56(14H), 7.84-8.06(4H), 8.68(2H) and 10.9-11.1 ppm (2H, NH), thus confirming successful synthesis of PAA-BO. The inherent viscosity of PAA-BO was 1.02 dL/g at a concentration of 0.5 g/dL in NMP at 30° C.

Example 1

Preparation of PAA-BT Modified Au Electrode (PAA-BT/Au)

0.05 g of PAA-BT obtained from <Preparation Example 1> was dissolved in 3 mL of NMP to obtain a polyamic acid solution. One μL of the polyamic acid solution was dropped onto an Au disk electrode (0.196 $cm^2$) and dried in a vacuum aspirator at 50° C. for 5 hours.

Example 2

Preparation of PAA-BO Modified Au Electrode (PAA-BO/Au)

The preparation method for PAA-BO/Au was similar to that for PAA-BT/Au electrode in <Example 1>, except that PAA-BT was substituted with PAA-BO obtained from <Preparation Example 2>.

Example 3

Preparation of Three Dimensional (3D) PAA-BO Modified Au Electrodes (3D-PAA-BO/Au)

To prepare a three-dimensional PAA-BO modified Au (3D-PAA-BO/Au) electrode, 0.05 g of PAA-BO obtained from <Preparation Example 2> was dissolved in 3 mL of NMP to form a polymer solution, followed by precipitation in 50 mL of stirred acetone. After centrifugation at 5500 rpm for 1 minute, the precipitate was washed with acetone. The final precipitate was dispersed into 3 mL acetone to form a suspension. 1 mL of the suspension was dropped onto an Au disk electrode (0.196 cm$^2$) and dried in a vacuum aspirator at 50t for 5 hours.

Figure 1:
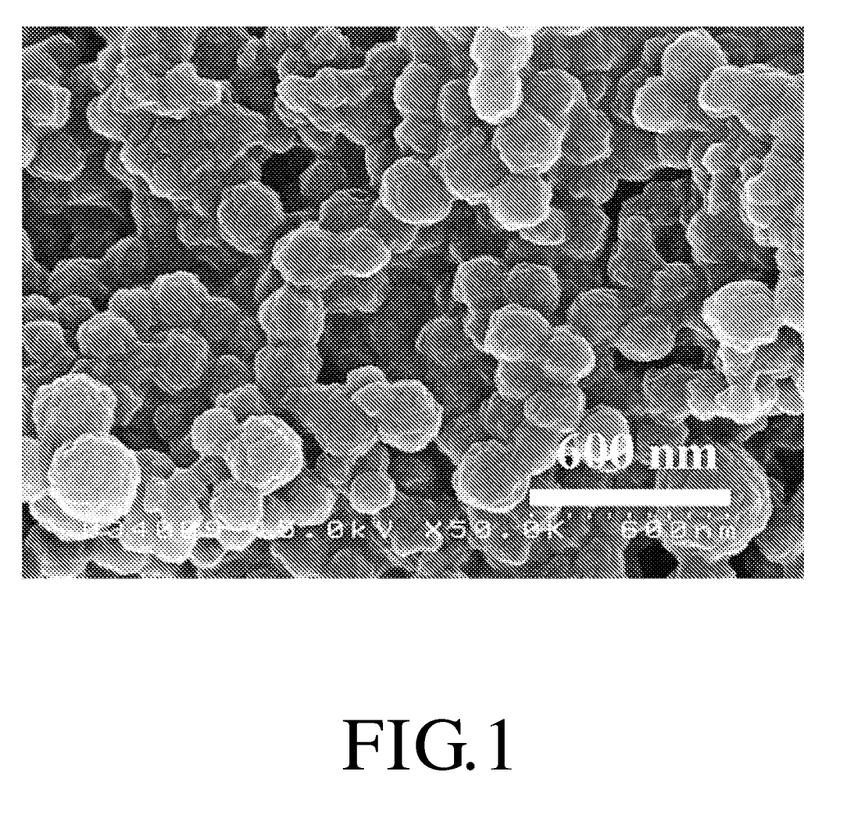
FIG. 1 is a scanning electron microscope (SEM) photograph of a 3D-PAA-BO/Au electrode of this invention.

Referring to FIG. 1, the surface of the 3D-PAA-BO/Au electrode exhibited nanometer-pores under a scanning electron microscope (SEM). This is presumably that, due to the mixing of the polymer solution with acetone, the polyamic polymer chains become entangled and remain suspended in the solvent. This results in the aggregation of PAA-BO particles and the formation of a granular three-dimensional structure.

<Electrochemical Measurements>

Electrochemical measurements were performed on an electrochemical workstation (CH Instruments, USA. Model number: CHI 660A) with a three-electrode system having either one of the PAA-BT/Au, PAA-BO/Au or 3D-PAA-BO/Au electrode obtained from Examples 1 to 3, a bare Au electrode, and an Ag/AgCl electrode as working, counter, and reference electrodes respectively.

All electrochemical measurements were performed in 40 mL of 0.2 M phosphate buffer solution (PBS, pH 7.0) at 25° C., with an applied potential of −0.5 V. 0.1 mL of different concentrations of $H_2O_2$ solution was sequentially added (from low to high) into PBS. The current during the test was recorded, and the relationship between the current vs. time or response current vs. $H_2O_2$ concentration were plotted.

All measurements, including detection limit, linear range and sensitivity, were taken when the electrode is responsive to each concentration change with a signal to noise ratio of at least 3. The sensitivity for $H_2O_2$ was also studied and was a ratio of the slope of the curve of the current vs. $H_2O_2$ concentration plot to the surface area of the Au electrode.

The results of the electrochemical measurements of PAA-BT/Au, PAA-BO/Au and 3D-PAA-BO/Au are listed in Table 1.

TABLE 1

|  | Example 1 | Example 2 | Example 3 |
|---|---|---|---|
| Electrode | PAA-BT/Au | PAA-BO/Au | 3D-PAA-BO/Au |
| Response time (seconds) | 5.2 | 3.9 | 1.9 |
| Detection limit (μM) | 4.9 | 5.0 | 1.43 |
| Linear range (mM) | 0.025-5.0 | 0.025-2.5 | 0.00625-2.5 |
| Sensitivity (μA/mM · cm$^2$) | 280.6 | 311.2 | 1394.9 |

Figure 2:
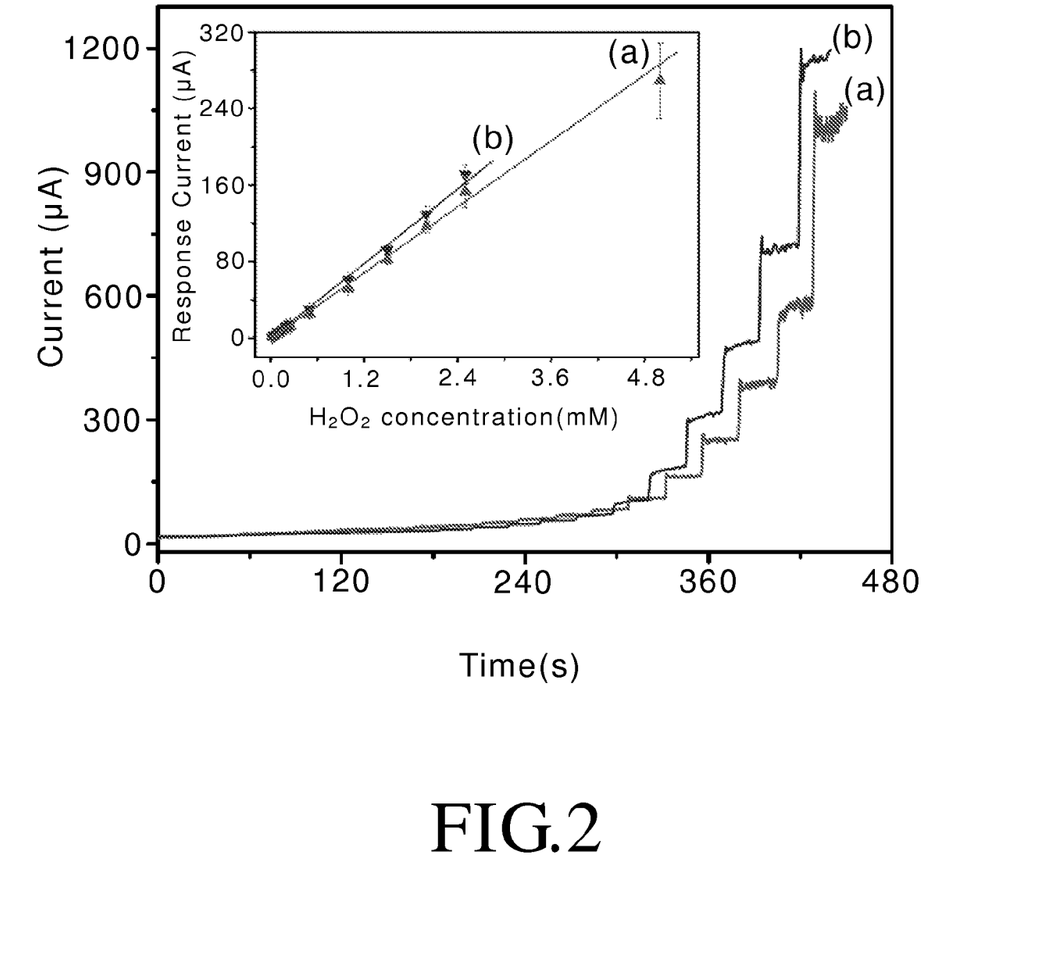
FIG. 2 is a current-time plot of (a) PAA-BT/Au and (b) PAA-BO/Au electrodes after successive addition of increasing concentrations of $H_2O_2$. Inset: linear dependence of response current v.s. $H_2O_2$ concentration for the (a) PAA-BT/Au and (b) PAA-BO/Au electrodes.
Figure 3:
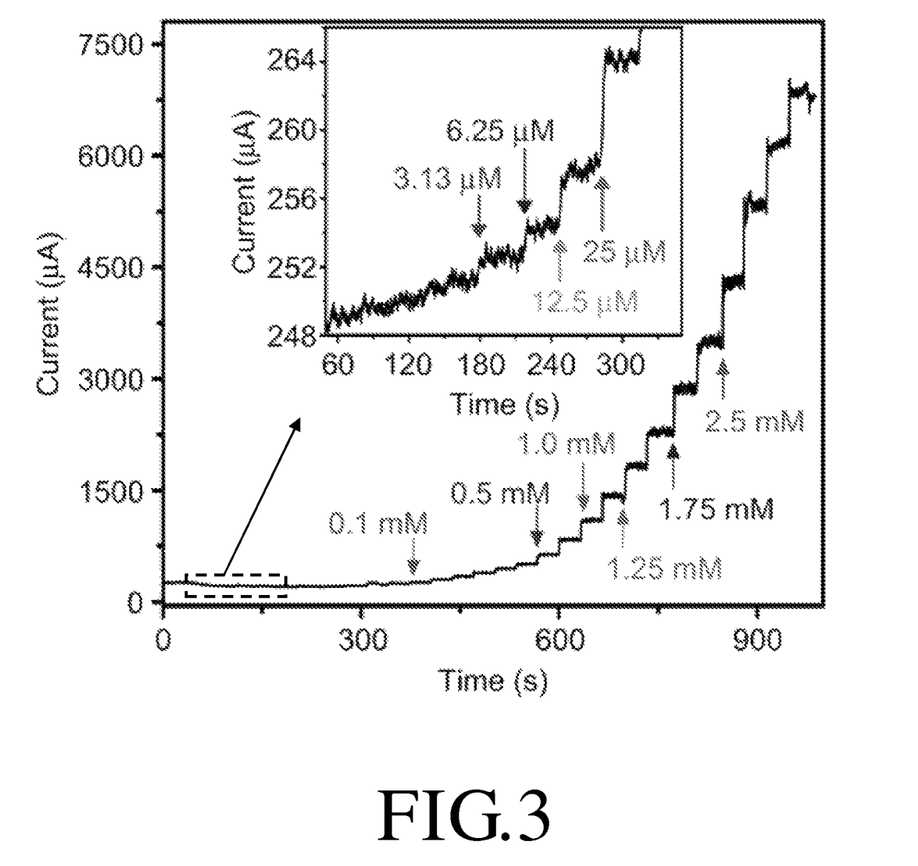
FIG. 3 is a current-time plot of the 3D-PAA-BO/Au electrode after successive addition of increasing concentrations of $H_2O_2$. Inset: enlarged plot for a square region circumscribed by dashed line.

As shown in FIGS. 2 and 3, when 1 mL of $H_2O_2$ was added to PBS with a successive increase in concentration, the response currents of PAA-BT/Au and PAA-BO/Au electrode increased.

In FIG. 2, curves a and b represent PAA-BT/Au and PAA-BO/Au electrodes, respectively. The electrode response was rapid and sensitive, reaching approximately 95% of the steady-state current less than 5.2 s after each addition of $H_2O_2$. The inset of FIG. 2 is a plot showing the current response to $H_2O_2$ being linear over a range from 25 μM to 5 mM, with a sensitivity of 280.6 mA/mM·cm$^2$ (Table 1 and FIG. 2, inset).

FIG. 3 is a current-time plot of the 3D-PAA-BO/Au electrode, showing a rapid response time, reaching approximately 95% of the steady-state current in about 1.9 seconds. The concentration shown on the plot indicates the final concentration of $H_2O_2$ after the electrochemical reaction reached equilibrium.

Figure 4:
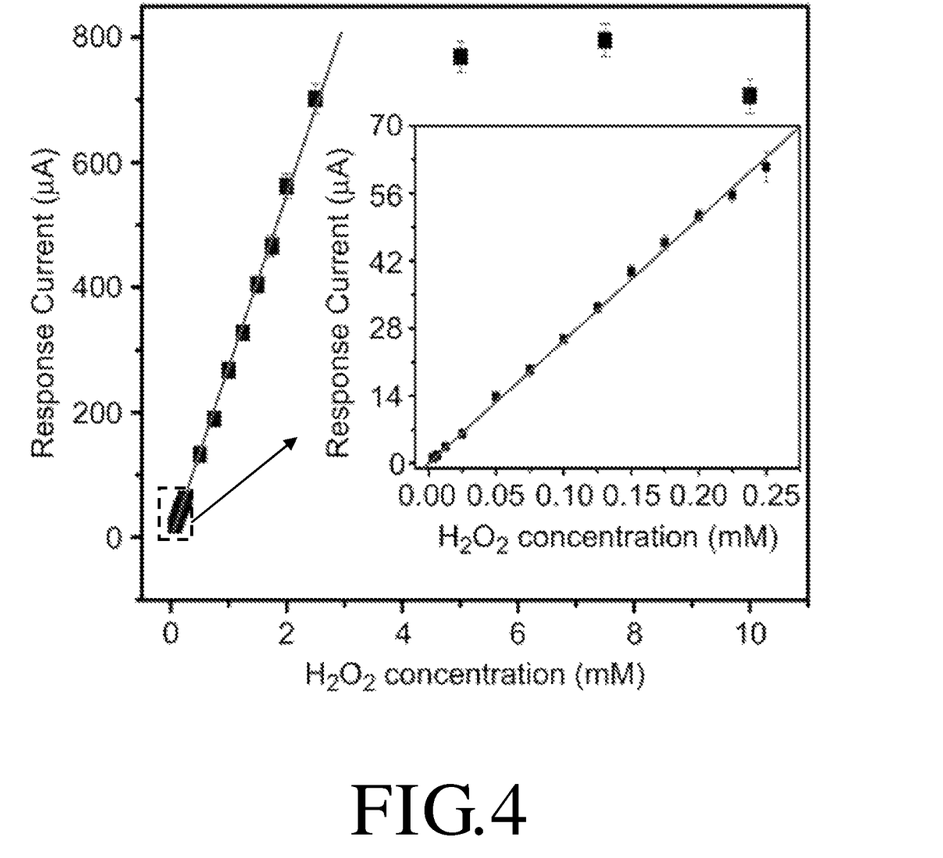
FIG. 4 is a current-$H_2O_2$ concentration plot of the 3D-PAA-BO/Au electrode showing the linear dependence of response current vs. $H_2O_2$ concentration. Inset: enlarged plot for a square region circumscribed by dashed line.

A plot of the response current vs. $H_2O_2$ concentration of the 3D-PAA-BO/Au electrode from Example 3 is shown in FIG. 4. The response of the 3D electrode to $H_2O_2$ was linear over a range from 6.25 μM to 2.5 mM. In addition, the increased surface area attributed to the 3D structure of the 3D-PAA-BO/Au electrode provides sensitivity of 1394.9 μA/mM·cm$^2$, approximately 4.5 times higher than that of PAA-BT/Au and PAA-BO/Au electrodes. The detection limit was also enhanced from 5.0 μM to 1.43 μM.

As shown in Table 1, 3D-PAA-BO/Au electrode has a shorter response time, lower detection limit and higher sensitivity when compared to PAA-BT/Au or PAA-BO/Au. This is presumably because the $H_2O_2$ could diffuse through the granulated surface freely.

<Interference Testing>

All electrochemical measurements were performed in 40 mL of 0.2 M PBS (pH 7.0) at 25° C. An applied potential of −0.5 V was used for the following experiment. After current stabilized, 1 mM $H_2O_2$ solution was added in a phosphate buffer of PAA-BT/Au. After current stabilized, 0.1 mL of each of the interfering molecules, i.e., ascorbic acid (AA) and uric acid (UA), was added at an interval of every 40 seconds. The addition sequence of the interfering molecules was in the following specified order: 0.1 mM of AA, 0.1 mM of UA, 1 mM of AA, and 1 mM of UA. The concentration of each of the interfering molecules is the final concentration after each of the interfering molecules was added into the 40 mL of 0.2 M PBS.

Figure 5:
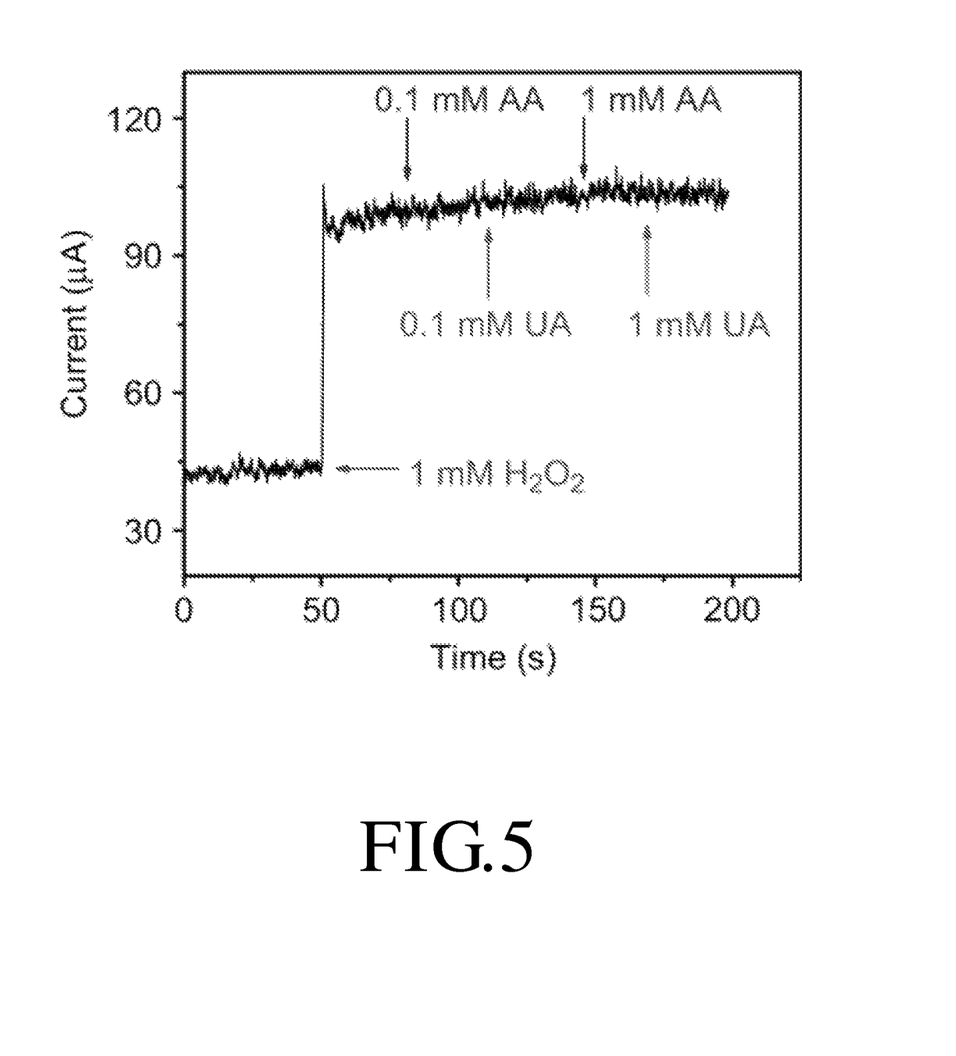
FIG. 5 is a plot showing the effects of interfering molecules, i.e., ascorbic acid and uric acid, on the response currents of PAA-BT/Au.
Figure 6:
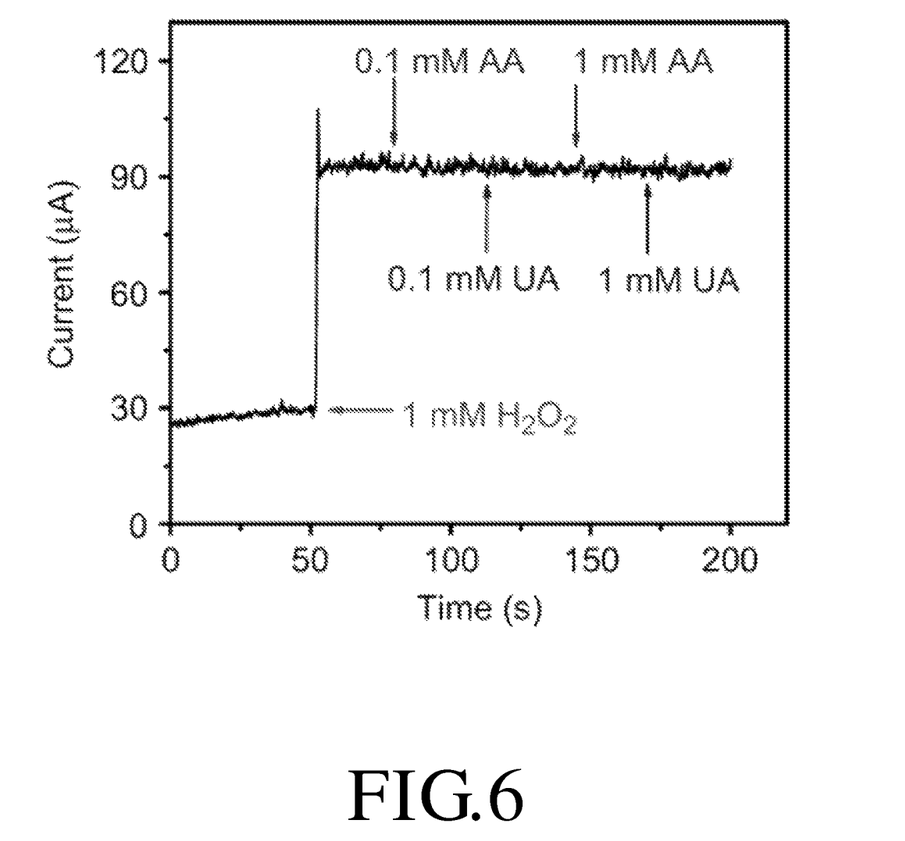
FIG. 6 is a plot showing the effects of interfering molecules, i.e., ascorbic acid and uric acid, on the response currents of PAA-BO/Au.

FIGS. 5 and 6 show the effects of the interfering molecules on the response currents of PAA-BT/Au and PAA-BO/Au, respectively. The addition of AA and UA had no effect on the current responses to $H_2O_2$, indicating that these electrodes are highly selective.

To sum up, the electrode having polyamic acid of formula (I) can detect $H_2O_2$ at reduction potential. In addition, it has shorter response time (as low as 1.9 seconds), lower detecting limit (as low as 1.43 μM) and higher sensitivity (as high as 1394.9 μA/mM·cm$^2$).

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

What is claimed is:

1. A polyamic acid of formula (I):

wherein each Z independently is in which each R independently is hydrogen, a phenyl group, or a $C_1$ to $C_{12}$ alkyl group; each bond a independently is at position 4 or 5;

each bond b independently is at position 4' or 5'; M is —S—, —O—, —CH$_2$—,

$R^5$ being —SO$_3$H, or a $C_1$ to $C_{12}$ alkyl group;
m is 1 or 2, when m is 1, Y is when m is 2, Y is X is O or S;
each of $R^1$, $R^2$, $R^3$, and $R^4$, independently, is hydrogen, a $C_1$ to $C_{12}$ alkyl group, a $C_1$ to $C_{12}$ alkoxy group, a $C_1$ to $C_{12}$ ether group, a $C_1$ to $C_{12}$ cyclic alkoxy group, halogen atom, a $C_1$ to $C_{12}$ haloalky group, a hydroxyl group, a trifluoromethoxy group, a trifluoromethyl group, or a phenyl group; and
n is an integer ranging from 5 to 1000.

2. The polyamic acid of claim 1, wherein m is 2, and Y is

3. The polyamic acid of claim 1, wherein Z is

4. The polyamic acid of claim 1, wherein each of $R^1$, $R^2$, $R^3$, and $R^4$ is hydrogen.

5. The polyamic acid of claim 2, wherein each of $R^1$, $R^2$, $R^3$, and $R^4$ is hydrogen.

6. An electrode for an electrochemical device, comprising:
a conductor; and
an active layer on said conductor and including polyamic acid of claim 1.

7. The electrode of claim 6, wherein said active layer contains a plurality of nano-meter pores.

8. The electrode of claim 6, suitable for detecting hydrogen peroxide or organic peroxy acid.

9. The electrode of claim 8, wherein said organic peroxy acid is percarboxylic acid.

* * * * *